United States Patent
Pietrocola et al.

(10) Patent No.: US 11,170,626 B2
(45) Date of Patent: Nov. 9, 2021

(54) AUTOMATED ENVIRONMENT HAZARD DETECTION

(71) Applicant: Luvozo PBC, Brookeville, MD (US)

(72) Inventors: David Pietrocola, Washington, DC (US); Terrance Jude Kessler, Alexandria, VA (US); Mohammed Samer Charifa, Rockville, MD (US); Babatunde O. Ogunfemi, Arlington, VA (US)

(73) Assignee: Luvozo PBC, Brookeville, MD (US)

( * ) Notice: Subject to any disclaimer, the term of this patent is extended or adjusted under 35 U.S.C. 154(b) by 457 days.

(21) Appl. No.: 15/268,228

(22) Filed: Sep. 16, 2016

(65) Prior Publication Data

US 2017/0140631 A1 May 18, 2017

Related U.S. Application Data

(60) Provisional application No. 62/219,899, filed on Sep. 17, 2015.

(51) Int. Cl.
| | |
|---|---|
| *G08B 21/04* | (2006.01) |
| *A61B 5/00* | (2006.01) |
| *A61B 5/11* | (2006.01) |
| *G16H 40/63* | (2018.01) |
| *G01C 21/20* | (2006.01) |

(Continued)

(52) U.S. Cl.
CPC ............ *G08B 21/0476* (2013.01); *A61B 5/00* (2013.01); *A61B 5/1117* (2013.01); *A61B 5/7275* (2013.01); *G01C 21/206* (2013.01); *G01J 1/4204* (2013.01); *G06N 3/0436* (2013.01); *G08B 31/00* (2013.01); *G16H 40/63* (2018.01); *A61B 5/7264* (2013.01); *A61B 2505/07* (2013.01); *A61B 2560/0242* (2013.01)

(58) Field of Classification Search
CPC ... G01C 21/206; G01J 1/4204; G06N 3/0436; G08B 21/0476; G08B 31/00
See application file for complete search history.

(56) References Cited

U.S. PATENT DOCUMENTS

| | | |
|---|---|---|
| 8,529,448 B2 | 9/2013 | McNair |
| 8,823,526 B2 | 9/2014 | Kaiser et al. |

(Continued)

FOREIGN PATENT DOCUMENTS

| | | |
|---|---|---|
| WO | WO-2009001057 A1 | 12/2008 |
| WO | WO-2014032181 A1 | 3/2014 |
| WO | WO-2014195146 A1 | 12/2014 |

OTHER PUBLICATIONS

Dai, J., et al., "Mobile phone-based pervasive fall detection," Personal and Ubiquitous Computing, vol. 14, Issue 7, pp. 633-643 (Oct. 2010).

(Continued)

*Primary Examiner* — Nader Bolourchi
(74) *Attorney, Agent, or Firm* — Butzel Long

(57) ABSTRACT

Systems and techniques are provided in which one or more environmental sensors collect data about an environment. An environmental hazard assessment module collects and analyzes data obtained by the environmental sensors to automatically identify, categorize, and/or rate the severity of potential environmental hazards. The hazards are provided to a user for a particular region of the environment or for a larger environment that includes multiple regions.

20 Claims, 10 Drawing Sheets

(51) Int. Cl.
G01J 1/42 (2006.01)
G06N 3/04 (2006.01)
G08B 31/00 (2006.01)

(56) References Cited

U.S. PATENT DOCUMENTS

| | | |
|---|---|---|
| 8,974,403 B2 | 3/2015 | Yang et al. |
| 9,036,019 B2 | 5/2015 | Hanson et al. |
| 2012/0075464 A1 | 3/2012 | Derenne et al. |
| 2013/0285813 A1 | 10/2013 | Kasama |
| 2013/0297542 A1 | 11/2013 | Piekniewski et al. |
| 2015/0260514 A1* | 9/2015 | Menelas ............... A43B 3/0005 702/2 |
| 2016/0113551 A1* | 4/2016 | Annegarn ............. A61B 5/1117 600/595 |

OTHER PUBLICATIONS

International Search Report and Written Opinion dated Dec. 12, 2016 as received in Application No. PCT/US2016/052288.

* cited by examiner

AUTOMATED ENVIRONMENT HAZARD DETECTION

CROSS-REFERENCE TO RELATED APPLICATIONS

This application claims the benefit of U.S. Provisional Application Ser. No. 62/219,899, filed Sep. 17, 2015, the disclosure of which is incorporated by reference in its entirety.

BACKGROUND

One in three Americans over the age of 65 experience a fall each year and 2.4 million end up in the emergency room as a result. Falls are the number one cause of death for older adults due to injury. Costs associated with falls are estimated to be at least $30 billion and will reach $55 billion by 2020 according to the Centers for Disease Control and Prevention. Falls impact older adults, whose fear of falling alone affects quality of life; family caregivers, who worry about their parents' safety; and senior living facilities and care providers, which need to ensure a safe environment. Research indicates that the most common cause of falls among the elderly is due to environmental hazards. In addition, environmental hazards may cause injury or potential injury in many other situations, such as where small children are present, where a region is difficult to navigate regardless of the person's age or ability, or where there are inherent environmental hazards in a region that can be mitigated, but in some cases not entirely removed.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Figure 1:
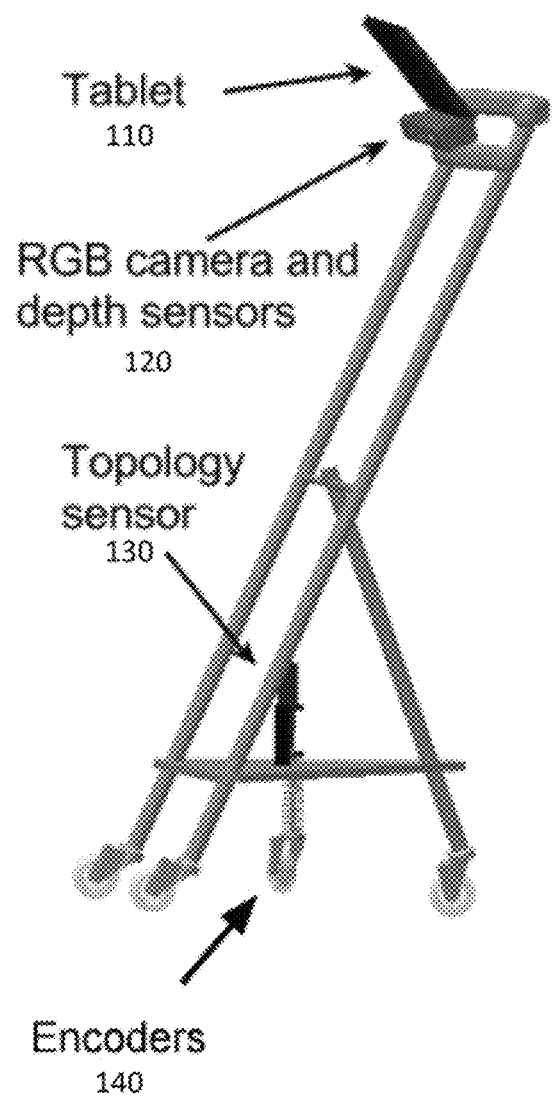
FIG. 1 shows an example of a device according to an embodiment of the invention.

Environmental hazards such as fall hazards typically are identified and evaluated by human evaluators, who perform such an analysis of a particular area using personal knowledge and training. Results of such evaluations may vary greatly depending upon the particular person that performs the analysis, the time and extent of the evaluation, and the like. Accordingly, there is a need for automated systems to identify, evaluate, and classify environmental hazards such as fall hazards, to improve the uniformity, reliability, and accuracy of such assessments. Disclosed herein are systems and techniques for automated environmental hazard assessment, such as for use in the home and other indoor spaces. For example, embodiments disclosed herein may provide automated systems and methods to perform an analysis of fall hazards within a home. Potential fall hazards and/or other environmental hazards may be identified, classified based on the level of the hazard, and solutions to reduce or eliminate the severity of the hazards may be provided.

For example, a sensor suite may be used to identify common but non-obvious environmental hazards, such as hazards that may trigger falls by older adults, individuals recovering from surgery, and the like. Such hazards may include, but are not limited to, low lighting, floor transitions, obstacles, wet floors, poor spacing, trip hazards, and the like. As another example, embodiments disclosed herein may identify environmental hazards that may present a danger to infants, young children, or the like, such as obstacles, furniture that may tip easily, stairs, floor transitions, and the like. Once a potential hazard has been identified, the potential risk that it will cause a fall or other harm is determined. Such an assessment may be based on, for example, additional sensor data, fall statistics, and personal ability. When a potential hazard has been confirmed as a hazard, it may be given a rating indicating the level of danger, the reason for the danger, and a list of possible interventions that may require an onsite trained expert. After action has been taken to mitigate the hazard the assessment can be initiated again to verify if the environmental condition has improved or if the hazard is still present.

In an embodiment, a mechanical system may be used to acquire environmental information. The mechanical system may include, or may be used in conjunction with, one or more environmental sensors.

In an embodiment, methods and systems disclosed herein may identify environmental hazards that may trigger, or be likely to trigger, falls in older adults. Systems disclosed herein may efficiently replicate an assessment that typically would be performed by a falls specialist, and may serve as an efficient and accurate alternative to expert in-home assessments by trained specialists.

In an embodiment, a user interface may be provided via which an operator can provide data about an individual or type of individual expected to be presented within a particular environment, as well as providing output about environmental hazards detected and assessed by the system. The input interface may be, for example, any audio or visual system capable of indicating the results of fall hazard assessment. Once a hazard is identified and/or assessment completed for an individual hazard or an entire environment, the results and/or recommendations may be output to a dashboard or database. In some embodiments this interface may be the same device used to acquire sensory data such as cell phone, tablet, computer, or robotic system. Alternatively or in addition, the information may be displayed remotely by a secondary device such as any a computer located in the same location as the assessment system, or in a remote location connected to the assessment system such as via the Internet.

Embodiments disclosed herein may use a range of mechanical, solid state, optical, and other sensors to detect environmental conditions such as lighting level, floor transitions, obstacles, trip hazards, and the like. For example, embodiments may include or use a light sensor, a digital camera, a physical height gauge, a depth sensor, and the like. As a specific example, a light sensor or digital camera may be used to detect a low lighting condition. As another example, a physical height gauge may be used to detect floor transitions. As another example, a physical touch sensor, depth sensor, and/or digital camera may be used to detect obstacles and trip hazards. As another example, the size and shape of an object may be determined using one or more RGB sensors and/or depth sensors, after which the object may be classified according to the likelihood that it presents a hazard.

Embodiments disclosed herein also may include a computer to process environmental information. The computer may be provided by, for example, a hand held device such as cell phone, tablet, or the like, or any other type of computer, or remote or distributed processing.

Embodiments disclosed herein may be implemented on any suitable platform, such as a handheld device, a portable sensor suite and/or computing device, a fully automated robotic system capable of self navigation, or the like.

FIG. 1 shows an example of a device according to an embodiment of the invention. The device includes a portable frame on which one or more sensors may be mounted. For example, one or more RGB/depth sensors 120, and topology sensors 130 in communication with height encoders 140 may be mounted on the frame. The sensors may be in communication with a tablet 110 or other computing device that collects and analyzes environmental data from the sensors 120, 130. It will be understood that the specific physical arrangement of the device shown in FIG. 1 is illustrative only, and any other suitable configuration may be used. For example, various sensors may be mounted on a special-purpose device such as the frame shown in FIG. 1, an autonomous robot, an existing device such as a cleaning cart, robotic vacuum, or other device that routinely traverses a particular area. In some embodiments, only a portable device such as a tablet or smart phone may be used, and various sensors incorporated into the device may be used instead of the special-purpose sensors shown in FIG. 1. For example, an integrated camera may be used to obtain RGB, depth, object, or other environmental data.

More generally, any sensor disclosed herein may be used with any physical frame. In some embodiments, the sensors may be incorporated into a single portable device without a separate or additional frame, such as a tablet, smart phone, or other portable electronic device that is used alone. Furthermore, some embodiments may allow for such a device to be incorporated into an additional physical frame, such as for convenience or consistency in obtaining environmental data. For example, a tablet may be used to obtain environmental data as disclosed herein. The tablet further may be mounted on or otherwise incorporated into a physical frame such as a cart, to allow for consistent environmental data collection in a given region. As another example, a device may be provided that incorporates a computer containing sufficient sensors to perform hazard assessment that can autonomously or semi-autonomously move to observe the environment to perform hazard assessment. As another example, a device may include a sensor package and interface with one or more computer or personal portable device such as a cell phone either by direct or indirect connection. Such a device may include, or be connectable to, a subset of the necessary sensors with the computer or portable contains the remaining sensors such that the combination of the two is sufficient to perform assessment. FIG. 1 shows an example of such a device that includes topology, encoders, and depth sensors as previously disclosed, which can be combined with a tablet or similar device that provides RGB, IMU, or the like to form a user pushable environmental hazard assessment device with tablet user interface.

As previously described, a variety of sensors may be used to collect environmental data. Examples of such sensors will now be described in further detail. However, it will be understood that, more generally, the scope of the invention disclosed herein does not depend upon the specific sensor arrangement or arrangements used.

An RGB sensor may be provided by a digital camera, such as those commonly incorporated into tablets and smart phones. More generally, any device that uses imagery sensors such as CMOS or CCD sensors that transform light into digital information may provide RGB and/or depth environmental information.

A depth sensor may be provided by a digital camera as disclosed with respect to the RGB sensor. Any suitable algorithm may be used to extract depth information from the data collected by one or more digital cameras or similar sensors. Alternatively or in addition, any sensor which provides an array of 3D depth information about the environment may provide depth environmental data, such as stereo vision systems that use two or more RGB cameras, devices using time of flight information or structured lighting techniques such as the Microsoft® Kinect® devices, sonar systems, interferometry sensors such as laser trackers, and the like.

Figure 2:
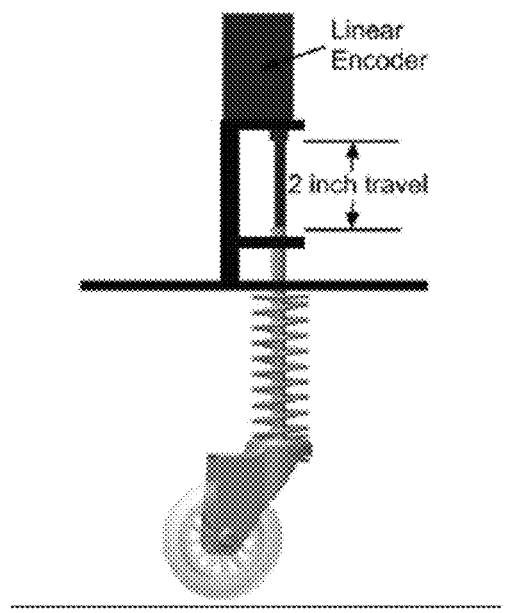
FIG. 2 shows an example of a gauge that includes a linear guide rail with a contact wheel that continually touches the floor surface according to an embodiment of the invention.

A topology sensor may be provided by any sensor capable of measuring a change in a local height of the floor that can occur for floor transitions, thresholds, missing tiles, or the like. FIG. 2 shows an example of a gauge that includes a linear guide rail with a contact wheel that continually touches the floor surface, in physical communication with a linear encoder that encodes any movement of the rail as a topology change. Topology environmental data also may be attained with a variety of other sensors such as depth sensors as previously disclosed, for example by using the sensor to directly measure floor height. Alternatively or in addition, height measurements may be made indirectly by detecting a change in a measurement of a device position or angle relative to the floor such as by an electronic level, accelerometer, IMU, or the like.

A wet floor sensor may be provided by any sensor capable of detecting the presence of liquid on a floor. Examples of such sensors include, for example, sensors that directly touch the floor and measure conductivity, sensors capable of passive optical observation by RGB or RGB-D, sensors that provide measurements of any change in reflectivity from known light source angle and wavelength, and the like.

As previously described, the environmental data collected by a platform and/or one or more environmental sensors may be processed to identify, classify, and/or rank environmental hazards. An embodiment may include several high-level components: an environmental hazard recognition algorithm that may automatically and/or autonomously detect potential common hazards, such as hazards that may contribute to falls, including floor clutter, low lighting, floor transitions, and the like; a continuous risk model that may provide facility- and/or resident-specific risk models that assess potential detected hazards and contextual data to determine relative risk and potential interventions; and a socio-technical component that may test and iterate intervention strategies for removing environmental fall hazards.

Figure 3:
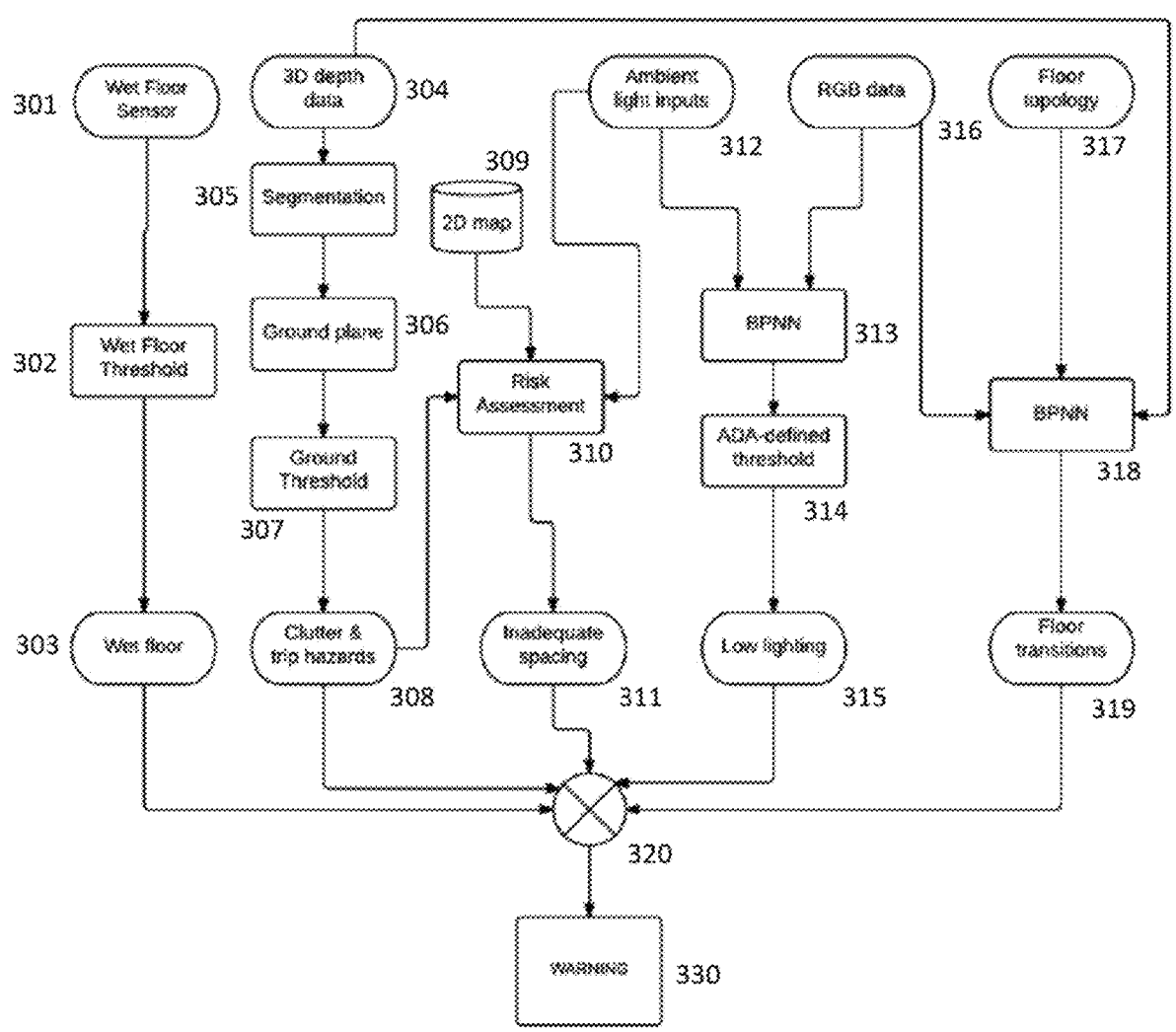
FIG. 3 shows an example subsystem and process arrangement to provide a hazard detection algorithm that uses sensors to identify potential environmental hazards according to an embodiment of the invention.

FIG. 3 shows an example subsystem and process arrangement to provide a hazard detection algorithm that uses sensors to identify potential environmental hazards for interventions according to an embodiment of the invention. By using a variety of mature algorithms such as BPNN (Back-propagation Neural Network), embodiments disclosed herein may detect several environmental hazards such as clutter, lighting, wet floor and floor transitions. The particular arrangement of components and subsystems shown in FIG. 3 is illustrative only, and other environmental hazards may be detected using a corresponding analysis tailored to the specific hazard to be detected. An example of each component will now be provided. However, various embodiments may use all or fewer than all of the components disclosed herein to determine the presence or degree of a potential environmental hazard.

At 301, a wet floor sensor may obtain information about an environment that indicates the possibility of a wet floor or similar potential hazard. For example, as previously disclosed, a wet floor sensor may obtain conductivity, reflectivity, or similar data in a region that indicates the possibility of a wet floor. The data may be assigned a value indicating the likelihood that it indicates a region in which the floor is wet. At 302, the collected data is compared to a threshold that may be preset, determined based on historic data, or obtained from any other suitable source. If the data meets or exceeds the threshold, the system may determine that a wet floor condition is present in the environment at 303.

In an embodiment, clutter or similar environmental hazards may be detected using a combination of 2D color information from one or more RGB sensors and 3D depth information from one or more depth sensors at 304. The region being evaluated may be divided into multiple segments at 305 and, for each segment, at 306 a ground plane may be identified which will be considered to act as a support plane for any potential fall hazard such as a clutter object above ground level, a crack on the floor, raised floor transitions, or the like. In embodiments in which the depth sensor is fixed on a mobile platform, this relatively computationally-intensive step may be needed only once during initialization for residences, rooms, corridors, or other areas of an environment. The ground plane may be identified using any suitable technique or algorithm. As a specific example, a random sample consensus (RANSAC) algorithm may be used to estimate the ground plane. In such an embodiment, three non-collinear points $\{p_i, p_j, p_k\}$ are randomly selected from point cloud P, one from a different quadrant of an image of the environment. Model coefficients are determined from the three points in $ax+by+cz+d=0$. The distances from all points $p \in P$ to the plane model (a, b, c, d) are determined. The number of points $p^* \in P$ with a distance d to the plane model is within a specified threshold are counted. Each set of points $p^*$ is stored and these steps are repeated for k iterations. The number of iterations may be chosen to be sufficiently high to provide a maximum success probability, such as 99%. After the algorithm is terminated, the set with the largest number of points (inliers) is selected as the best planar model found. For the selected $p^* \in P$, the planar model coefficients are estimated in a least-squares fashion, and a bounding 2D convex hull can be estimated for the ground plane. Since a horizontal plane is desired as the ground plane, the normal of the resulting ground plane must be parallel with the global z-axis.

After determining a ground plane surface at 306, the parameters (a, b, c) may be computed, for example by computing the height $h=z+(ax+by+d)/c$. For h greater than a ground threshold $\delta$ at 307, the corresponding point p is assigned to an above-ground height obstacle. Similarly, for $h<-\delta$, p is assigned as a point associated with a below-ground obstacle. Otherwise p is assigned as a ground-level point. Typical values for the ground threshold $\delta$ include 1-5 cm, though more generally $\delta$ may be set to any desired value (i.e., any z distance relative to the ground plane). At 308, groups of points may be identified, such as via a clustering algorithm or similar technique, and identified as environmental hazards, such as clutter or other trip hazards or the like.

In some embodiments, one or more data sources may be used in the identification, classification, and/or ranking of one or more environmental hazards. For example, ambient light data obtained from one or more ambient light sensors at 312 may be combined with a 2D map of an environment 309 and/or clutter identification 308 in a risk assessment 310. For example, the risk assessment may indicate locations in which an environment has inadequate spacing or other similar hazards at 311. As another example, RGB data 316 may be considered in combination with ambient light data 312, such as to determine whether an environment meets or exceeds a predefined threshold 314, such as a threshold set by ADA or other requirements. Such a determination may be made by any suitable comparison or other algorithm, such as a Backpropagation Neural Network (BPNN) as disclosed in further detail herein. The data also may be used to identify low lighting conditions 315 as disclosed in further detail herein.

Although some height-based environmental hazards, such as object, steps, and larger floor molding may be detected using this process, other types of potential hazards may be more difficult to detect. For example, relatively smooth floor transitions may present a fall hazard for some older adults, but may be difficult to detect using the combined 2D/3D analysis. In an embodiment, RGB or other digital camera data 316 and/or a special-use floor topology sensor may be used at 317 to detect floor transitions and other similar hazards. The data may be used individually or in conjunction with 3D depth data 304 as previously described. For example, to reliably measure change in floor height that occurs at floor transitions and thresholds, a floor topology sensor as shown in FIG. 2 may be used. A floor topology sensor as shown may include a linear guide rail with a contact wheel that is placed in continuous physical contact with the floor surface, and a linear encoder, such as the US Digital PE Linear Probe Encoder PE-500-2, to measure up to 1 inch in deviation in height relative to the plane of the platform wheelbase. The time-series sensor data feeds into a software filter and signal processing algorithm to detect step transitions as disclosed in further detail herein. Such a sensor may be useful, for example, to discover power cords or other cables that may be dangerously placed on or across pathways. Typically such cables may be difficult to detect with a conventional depth sensor due to their low profile. Floor topology, RGB, and/or 3D depth data may be analyzed to identify one or more floor transitions in an area. For example, a BPNN or similar processing technique may be trained and applied at 318. By identifying regions having data signatures matching signatures known to indicate floor transitions, such a technique may identify floor transitions in an environment at 319.

As a specific example, a digital camera may be used to detect color contrast at a transitional area where a height difference is report by a floor topology sensor. The presence of a color contrast may be used by a neural network classifier at 318 to detect a floor transition. For example, the following process may be used:
1—A small kernel (e.g., 64×64 or 32×32) is cropped from the center of a 2D image obtained by the RGB sensor.
2—The RGB color format data is converted into grayscale format.
3—A K-means algorithm is used to segment pixels in the image based on the light intensity values of the pixels into two areas representing, e.g., the two regions of the floor on either side of the transition.
4—A contrast difference $\Delta C(t_0)$ between the two areas is measured and stored in an array.
5—When a topology sensor detects a height difference $\Delta h(t_1)$, where time $t_1=t_0+S/d$, and S is the speed of the platform, for example, as estimated by an onboard IMU. Each value determined for $\Delta h(t_1)$ is provided to the neural network classifier with the associated $\Delta C(t_0)$ value.

An artificial neural network based classifier such as Support Vector Machine (SVM), Backpropagation Nerual Network (BPNN), Deap Neural Network (DNN), or the like, then may classify each identified floor transition based on a level of risk associated with the classification of transition. As a specific example, a standard Backpropagation Neural Network (BPNN) may be used to classify floor transitions into no risk, low risk, medium risk, or high risk floor transitions. Predetermined cases generally may be used as a training set for the neural network. Although BPNN is described as an illustrative example, any type of neural network or similar process may be used. In an example BPNN implementation, arbitrary values for initial weights W may be selected. The weights are multipliers which will be multiplied by each pixel intensity in the kernel to create a function which will output a confidence score for each of the risk levels. Without loss of generality, an example output vector in this embodiment is composed of four values, with each value corresponding to a confidence level for four cases, namely; No risk, Low risk, Medium risk and High risk floor transition. The goal of the BPNN is to optimize these arbitrarily weights so that they would accurately map input values (pixels intensity) to output values (risk levels). It is desirable for the behavior of this mapping function to minimize the error E during training. Initial outputs Y and errors E are calculated for the initial sets of weights. Derivatives of the error function E are calculated with respect to the weights. If increasing a given weight leads to an increased error, the weight is adjusted downwards and vice versa. This process is then iterated until there is a consistent small change in E for a selected threshold of changes in weights W.

Assuming that each input event vector X has dimensionality m, each output event vector has dimensionality n (with n=4 in the example embodiment described above), the network has N+n trainable neurons (with N having any value such that N≥m), and the central kernel of the image being analyzed has dimensions d×d, then the input vector X includes a d×d greyscale image, d×d depth map of the same area, $\Delta h(t_1)$ and $\Delta C(t_0)$).

In an embodiment, low lighting, low contrast, or other similar hazards may be identified at 315. Low lighting may be a useful hazard to identify because such conditions may be particularly dangerous, for example, for senior living residents with age-related vision impairments such as a yellowing hue, cataracts, and glaucoma. Additionally, quick transitions between light and dark rooms or corridors can trigger disorientation as the eyes take time to adjust, which often requires a longer adjustment period among many older adults. A COTS ambient light sensor may be specifically designed to approximate human eye response to estimate low lighting situations and ambient light transitions. As a specific example, a light-to-digital converter such as the TAOS TS2561 includes a broadband and infrared photodiode in comparison to poorer ambient light sensors that overestimate infrared light response in providing applicable readings. More generally, any light sensor may be used. Sensor readings are converted to the illuminance unit of Lux according to empirical results. Such responses may be provided in the configuration parameters of an off-the-shelf sensor, or they may be selected and stored in a special-purpose sensor. Significant lighting changes or low-lighting conditions determined through collected data are annotated with hazard and, if applicable, location information as they are provided to the risk assessment model disclosed in further detail herein.

Low contrast on walking paths may be of particular interest when it occurs in conjunction with a height difference such as a step or clutter, or a frictional change at a floor transition. Such an environment may present a relatively high-risk environmental hazard. For example, a low-contrast area with a height difference or fractional change may be more likely to lead to falls due to loss of balance. The Americans with Disabilities Act (ADA) Accessibility Guidelines recommends a typical 70% contrast between light and dark surfaces. In an embodiment, when a height difference or floor transition is detected based on the previously described techniques, the image region may be segmented and a contrast between features may be calculated. The Weber Contrast formula may be applied in a manner consistent with fall risk research:

$$C_W=(L_a-L_b)/L_b$$

where $L_a$ is the average luminance (intensity) of a small window of grayscale pixels within the region of interest for the clutter object or lighter floor partition, and $L_b$ is the average luminance of a small window of grayscale pixels for the neighbor region on the ground plane or darker floor partition. If the contrast value $C_w$ surpasses a selected threshold, its value and the approximate incident location may be provided to the risk assessment model. The threshold may be selected, for example, based on known or determined environmental hazard models or values used by environmental hazard consultants.

In an embodiment, the results of one or more of the foregoing data collection and analysis components may be provided to a fall assessment module 320, which analyzes this data as disclosed herein. If a hazardous condition is detected, one or more warnings may be provided to a user, recorded in a model of the region, or otherwise made available to a person evaluating the environment or using the environment at 330.

Figure 4:
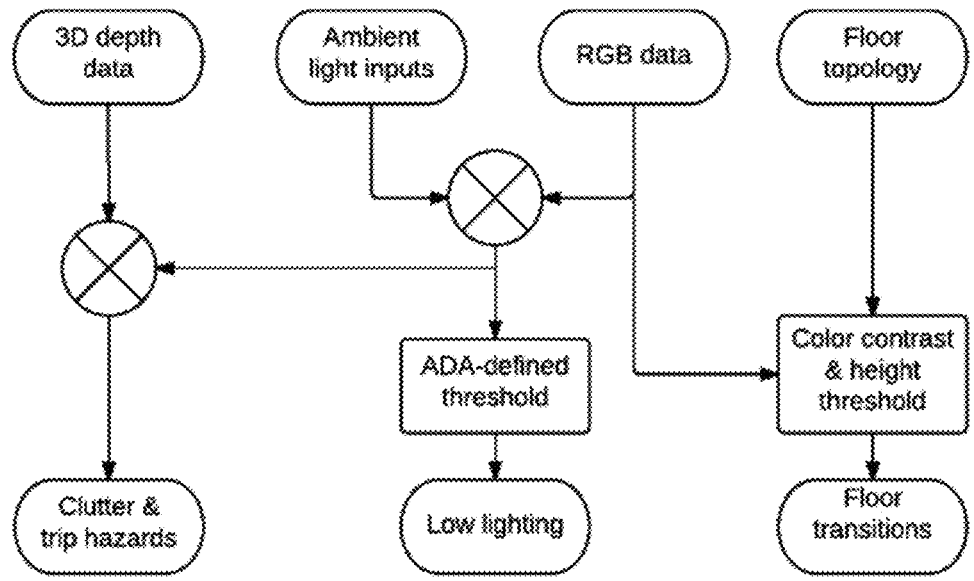
FIG. 4 an example subsystem and process arrangement to provide a hazard detection algorithm that uses sensors to identify potential environmental hazards according to an embodiment of the invention.

In some embodiments, a reduced or different set of sensors and environmental hazard detection techniques may be used. For example, in an embodiment designed for fall detection, environmental hazards may be divided into the following categories: clutter detection, narrow corridors, floor transitions, and low lighting. An example of such a hazard detection system is shown in FIG. 4. In this example, 3D depth data is used to identify clutter and trip hazards. Ambient light input and/or RGB data is used to identify low lighting conditions, for example, based upon ADA standards. Floor topology, optionally in combination with RGB data, may be used to identify floor transitions based upon color contrast and height thresholds as disclosed in further detail herein. More generally, when it is desired to detect a particular type of environmental hazard such as a fall hazard, a set of hazards or types of hazards that are relevant to detecting the particular environmental hazard may be used.

Figure 5:
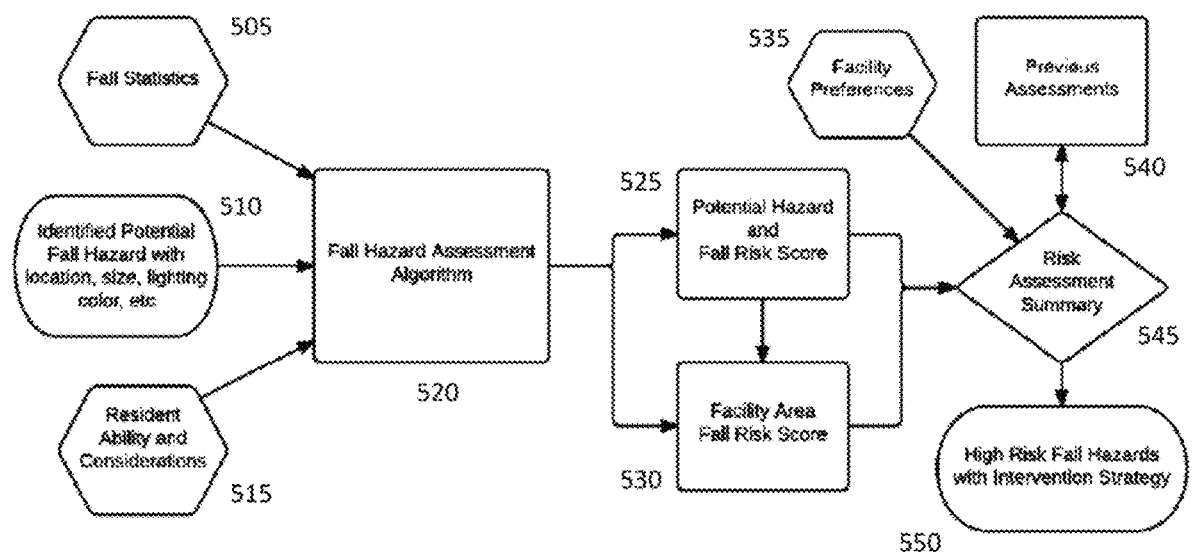
FIG. 5 shows an example of an environmental hazard assessment model according to an embodiment of the invention.

FIG. 5 shows an example of an environmental hazard assessment model as disclosed herein. The example shown in FIG. 5 is provided with respect to a fall hazard assessment, but it will be understood that the same or similar arrangements may be used to identify and evaluate other types of environmental hazards as previously disclosed. A hazard assessment model as disclosed may be implemented by an assessment module, which may be a computing device integrated with the sensing components described with respect to FIG. 3 such as a laptop, tablet, smart phone, or the like, or may be a separate and/or remote computing device such as a remote server or cloud-based service. A hazard assessment model 520 as disclosed herein may determine a score reflecting the probability of an injury or other undesirable effect resulting from the hazard. For example, when a hazard evaluation system as disclosed herein is used to evaluate fall hazards, the assessment model may assign a score that indicates the probability that a person will fall due to one or more identified hazards. The model may account for the identified potential hazard's location (if available), the size and/or visibility of the hazard, lighting, color, and the like 510, may account for known general fall statistics 505, and may also include an adjustment for a particular person's ability or other considerations 515 such as mobility, age, vision ability, and the like. If the score reaches a defined threshold, the hazard is confirmed and an intervention strategy may be suggested. In addition to detecting potential environmental hazards such as fall hazards, the associated indoor space may be scored as a whole and further areas may be defined, such as kitchen, dining room, loading dock, office, hallway, or the like. The assessment module may output the source of a potential hazard and the corresponding hazard rating number for the individual potential hazards as well as the total area rating.

In the example, environmental fall hazards are segmented into three groups: lighting, clutter, and floor transitions, as previously disclosed. For lighting hazards, an identified potential hazard may be compared to industry standards and user preferences to decide if and to what degree the condition presents a hazard. However, in some cases, floor transitions and clutter require more complex considerations.

The score for any individual potential fall hazard 525 may be calculated as a result of a function that considers the potential hazard's size, location with respect to walls and walking path, color, lighting with respect to the room, the statistical chance of falling from such a hazard, and the resident ability:

Identified Hazard Risk=Risk Function (Location, Size, Lighting, Color, Fall Statistics, Resident Ability)

Figure 7:
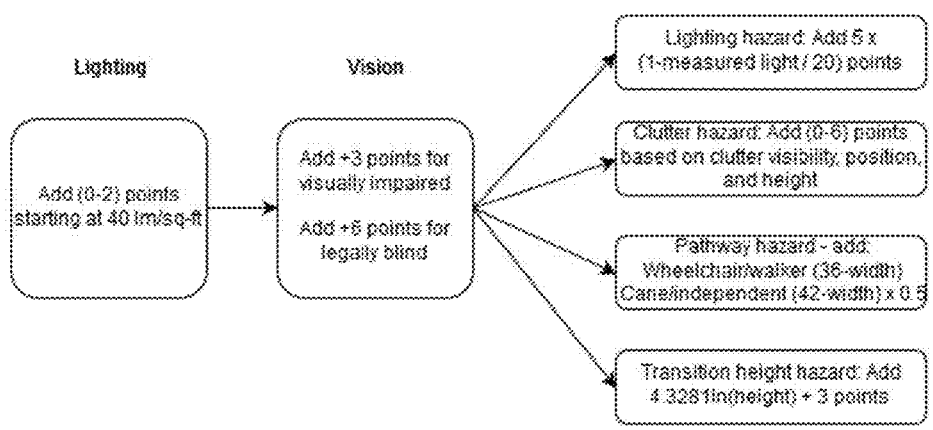
FIG. 7 shows an example of an environmental hazard algorithm according to an embodiment of the invention.
Figure 8:
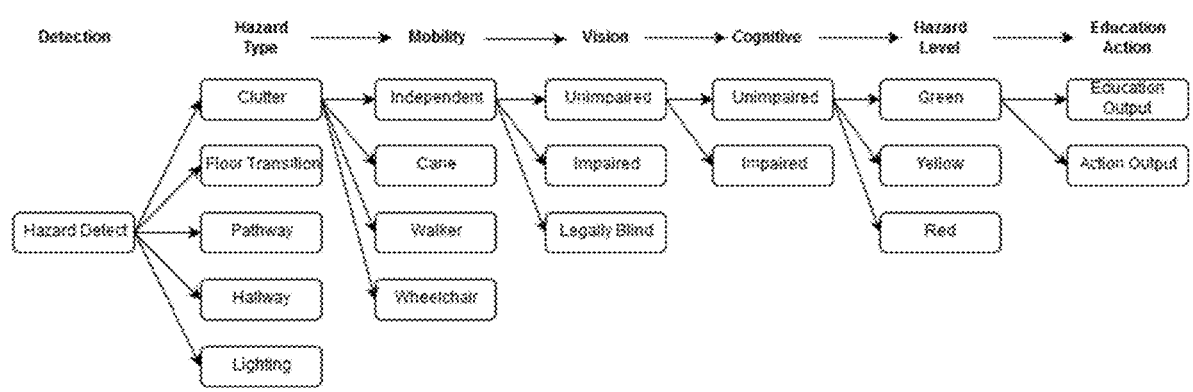
FIG. 8 shows an example of an environmental hazard scoring algorithm according to an embodiment of the invention.

For example, points may be assigned to each type of hazard based upon the severity of the potential hazard as well as other attributes of the environment and/or the hazard. A specific example of such a calculation is shown in FIG. 7 and discussed in further detail herein. Similarly, FIG. 8 shows an example of a tree representation showing how a detected hazard is assigned to an assessment, and an education or action.

Each area itself also may be assigned an environmental hazard risk score 530, such as a fall risk score. The area may be a region defined by the environment, such as a room, or may be defined by a user selection. The risk score may be based on lighting, contrast, and historical potential fall hazards within the area, for example, derived from a questionnaire with family member or other user. The total area risk score, as shown in the below equation, is the sum of the area fall risk score 530 and any identified potential hazard scores 525. In this example, the nominal area risk function reflects how easy it is to safely walk around the area.

Area Risk=Area risk function (Visibility, Fall Statistics, Resident Ability)+Identified Hazard Risk in Location A total space risk score for a region that encompasses multiple areas can be used to identify and assess fall risk trends over time. The total score may be, for example, a weighted sum of area risk functions. The weighting function for the sum is based on area-dependent fall statistics 540, and can be adjusted for the user preferences 535. For example, areas where many falls have historically occurred may assigned higher weights.

Total Space Risk=(Area RiskScore*Location Weighting function based on Resident Preference)

In an embodiment, an environmental hazard assessment model also may take into account assessing fall risk for older adults with different levels of capability, or an aggregation of abilities depending on space inhabitants (e.g. co-habitants). Poor vision, for example, could increase the weighting of lighting or contrast. On the other hand, total blindness would decrease the importance of lighting, color, or contrast, but could increase the weighting of support surfaces and obstacles. This individual fall risk assessment is even more important when the assessment results are used for intervention purposes.

In an embodiment, the results of the risk assessment process may provide an output summary at 550, which may include the total space score, area scores, and identified risks with associated risk scores. In some cases, recommendations to reduce or eliminate risks also may be provided. Such recommendations may be provided automatically, for example, based on a lookup table of known hazards and mitigation options matched against the identified hazards. As a specific example, in a fall assessment system, a floor height transition may be identified as being due to an area rug or similar feature. The system may recommend moving, altering, or marking the feature so as to reduce or eliminate the chance that a person walking through the area will trip and fall on the hazard, or will have an increase chance of seeing the hazard and thus avoiding it.

Embodiments of the presently disclosed subject matter may be implemented in and used with a variety of component and network architectures. A computing device suitable for implementing embodiments of the presently disclosed subject matter may be, for example, a desktop or laptop computer, or a mobile computing device such as a smart phone, tablet, or the like. The device may include a bus which interconnects major components of the computer, such as a central processor, one or more memories such as Random Access Memory (RAM), Read Only Memory (ROM), flash RAM, or the like, a user interface such as a display, a user input interface, which may include one or more controllers and associated user input devices such as a keyboard, mouse, touch screen, and the like, a fixed storage such as a hard drive, solid state drive, and the like, and a network interface capable of communicating with one or more remote devices via a suitable network connection.

The fixed storage may be integral with the computing device, or it may be separate and accessed through other interfaces. The network interface may provide a direct connection to a remote server via a wired or wireless connection, using any suitable technique and protocol as will be readily understood by one of skill in the art, including digital cellular telephone, WiFi, Bluetooth®, near-field, and the like. For example, the network interface 29 may allow the computer to communicate with other computers via one or more local, wide-area, or other communication networks.

More generally, various embodiments of the presently disclosed subject matter may include or be embodied in the form of computer-implemented processes and apparatuses for practicing those processes. Embodiments also may be embodied in the form of a computer program product having computer program code containing instructions embodied in non-transitory and/or tangible media, such as floppy diskettes, CD-ROMs, hard drives, USB (universal serial bus) drives, or any other machine readable storage medium, such that when the computer program code is loaded into and executed by a computer, the computer becomes an apparatus for practicing embodiments of the disclosed subject matter. Embodiments also may be embodied in the form of computer program code, for example, whether stored in a storage medium, loaded into and/or executed by a computer, or transmitted over some transmission medium, such as over electrical wiring or cabling, through fiber optics, or via electromagnetic radiation, such that when the computer program code is loaded into and executed by a computer, the computer becomes an apparatus for practicing embodiments of the disclosed subject matter. When implemented on a general-purpose microprocessor, the computer program code segments configure the microprocessor to create specific logic circuits.

In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions. Embodiments may be implemented using hardware that may include a processor, such as a general purpose microprocessor and/or an Application Specific Integrated Circuit (ASIC) that embodies all or part of the techniques according to embodiments of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to embodiments of the disclosed subject matter.

Experimental

Figure 6:
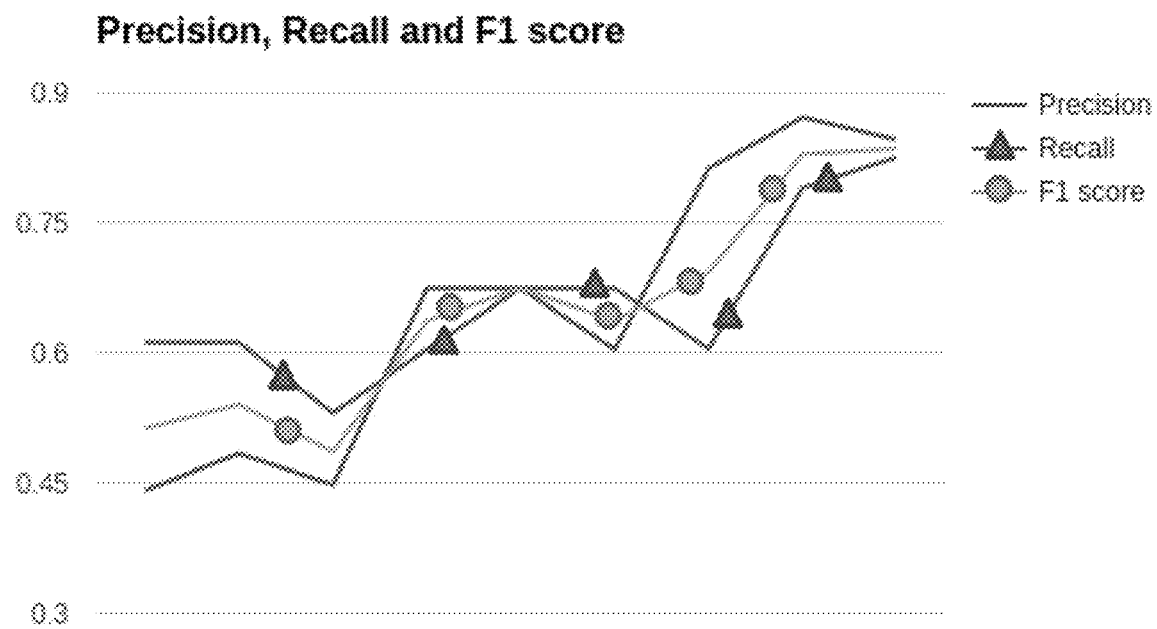
FIG. 6 shows precision, recall and F1 scores for a statistical segmentation approach according to an embodiment of the invention.

To examine and track progress of a hazard detection algorithm as disclosed herein, an accuracy testing framework was created to automate data-driven analysis. The second phase of data collection (simulated real-world home environments) were annotated for detectable hazards by a subject matter expert, including hazard type and attributes. The testing framework could then be used to quickly and efficiently evaluate how algorithm changes and parameter variations affected accuracy metrics. Following established classification algorithm testing practices, the framework generates precision, recall and F1 scores. FIG. 6 shows that F-score accuracy for detection of clutter and pathway hazards began at 50%, and approached 90% on the dataset as improvements progressed.

As previously disclosed, after a hazard has been identified a continuous risk assessment may be used to judge the severity of the hazard and provide a baseline to perform future assessments. In some cases it may be possible to use prior statistics on falls to determine which hazards have been the most prevalent—the more prevalent the hazard, the greater the score. However, in some cases the available data on falls may be either inconsistent or not recorded in a way that generates information useful in assessing randomly encountered specific hazards. Statistical observation also may not be in alignment with methods used by experts. One use of a scoring system as disclosed herein may be to provide a standard systematic method that gives a user a clearly-defined indication of a hazard danger.

To more closely approach the risk assessment that may be performed by a human expert, an algorithm that focuses on the procedure used to assess hazard may be used. Such an approach may take into account universal design elements, the personal abilities of the intended user, and certain specific metric of the observed hazard. In this example, universal design specifications define the ideal measurable environment. FIG. 7 shows an example of such a scoring algorithm, which is broken down into three sections of common environmental considerations, common person ability based, and individual hazards.

Person ability considerations were chosen to be vision, mobility, and cognitive impairment. Each of there is a major factor when performing an assessment and provide solid examples of how personal factors influence hazard considerations. For vision the three choices are unimpaired, impaired, and legally blind. Total blindness is combined and considered as legally blind for the scope of this proof of concept. Mobility is independent, cane, walker, and wheelchair. Cognitively either impaired or unimpaired. Impaired is not broken down further as that would require specific instructions from a caregiver. The term "impaired" is used here to indicate limited ability to properly judge and make choices in movement through a room.

The Environmental factor that applies equally to all hazards is room lighting. Lighting diminishes the ability to detect all hazards and contributes to each hazard the same way visual ability does. In a poorly lit room someone with impaired vision or is legally blind would see any hazard as a severe or color red hazard due to the lack of ability to see and avoid the hazard.

Pathways and hallways are based on design guidelines and personal mobility. Safe pathways and hallways come down to the width of the navigable path. Widths less than 36 and 42 inches for pathways and hallways respectively are considered hazardous. The narrower the pathway the greater the hazard danger. Mobility considerations determine how quickly the hazard changes from green to red and width decreases. Wheelchairs and walkers have greater with requirements than moving independently or with a cane is its own hazard.

Accordingly, in an embodiment, a narrow pathway or hallway may be identified as a hazard. From the previously-disclosed process of segmentation and clutter classification, there are two collections of data available: a collection of found clutter, and a collection of non-clutter segments. After filtering noise and merging improperly segmented items, given that anything left in the non-clutter collection does not satisfy the conditions for clutter, the remaining segments represent items that are large enough to be barriers possibly creating narrow pathways. From this point, each segment may be iteratively compares to each another segment, to determine if any two of these segments create narrow pathways (e.g., with a space of 36 inches or less) or narrow hallways (e.g., with a space between of 42 inches or less). For any found narrow hallways, the segments may be measured to determine if the segment heights are tall enough to be possible walls. Any narrow pathways or hallways so identified then may be added to the set of hazards, marked for any visual outputs, and all associated data may be stored.

Inadequate lighting contributes to all hazards but if the light level in a room drops below 20 lumens a lighting hazard is created. The darker the room the greater the hazard. The score for this hazard, like all hazards, is cumulative with both visual and general lighting contributions.

An unsafe threshold is defined as a height difference of at least one half inch. We have defined the minimum for this hazard to be one quarter of one inch. The reason for this is that the definition of one half in hazard height is more in line with a yellow hazard in our classification system. Additionally, thresholds under one half inch still cause falls. Scoring works such that every doubling in height over one quarter of one inch with increase the color of the hazard. For walkers and wheelchairs the one half inch height is red rather than yellow due to the height being a greater obstacle to roll over rather than step over.

In this example, clutter is the most complicated to score. The visibility of the color is critical. The ability to see the clutter and distinguish it from the surrounding area changes how dangerous the clutter is. The greater the visibility the lesser the danger. Similarly clutter that is harder to trip over may be less of a problem. Clutter that is closer to the wall may be less of a problem than out in the open.

One difficulty with clutter is that furniture may not be distinguished from other clutter. To account for this, clutter over 16 inches in height was assumed to be furniture. Furniture under 16 inches or considered to be like other clutter was marked for removal rather than relocation. Tall clutter under certain conditions was treated like a pathway.

Such a scoring system may provide a way to compare hazards in a measurable way. By providing a hazard score as in this example or in the previously-disclosed example techniques, a user may be motivated to work on the most dangerous hazards first. For example, a hazard score may be categorized into the three groups of green, yellow and red corresponding to increases in hazard danger, as shown in FIG. 8. The arrows in FIG. 8 show an example scoring path; however, it will be understood that in other embodiments different combinations of the same attributes may be used.

Recommended actions to mitigate environmental hazards may be specific to the hazard type, personal abilities, and hazard score. With five types or hazards, 24 configurations of personal settings, and three colors of hazard there are up to 360 different sets of recommendations and actions. Many of the cases are repetitive or restricted due to not allowable states. For example, in the scoring system illustrated in FIG. 8 there are no green hazards for a person with impaired vision. So in addition to having a different score and color, the recommended action also may be adjusted to match the situation and indicate how urgent it is to make a change.

In another evaluation, results of an automated hazard detection system as disclosed herein were compared against a cohort of physical therapists and occupational therapists with experience in conducting in-home assessments. Seven rooms were selected across three residences, with auxiliary rooms used for the previously discussed development set. These seven rooms (two living rooms, two kitchens, one bedroom, one home office, one hallway) were then combined with a scenario describing a resident's physical limitations (if any) and use of assistive devices (if any). A walkthrough video was recorded for each room and presented as an online survey, an approach consistent with the literature. Following each video collection, an automated fall assessment system (AFAS) as disclosed herein cart collected raw sensor data from the RGB-D, topology, and ambient light sensors at 1 Hz for each room walkthrough. Three PTs and three OTs with about 1-20 years of experience completed the survey, identifying a total of 45 hazards. Detections that matched a hazard flagged by an expert were counted as a true positive, while all others were counted as false positives.

Figure 9:
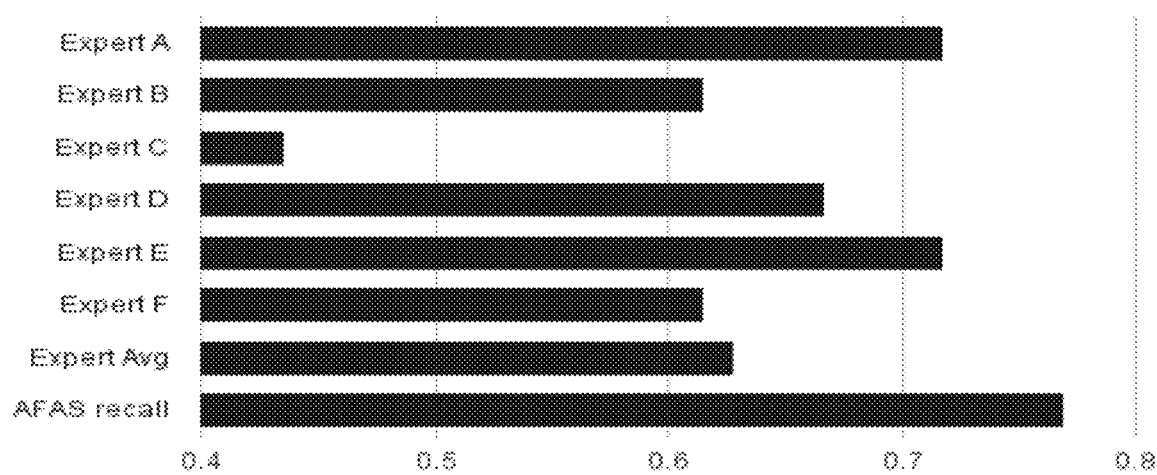
FIG. 9 shows a comparison of results of an automated hazard detection system analysis according to an embodiment of the invention, compared to hazard analysis performed by human evaluators.

Overall, in evaluating true positive detections, AFAS performed better on average than each individual expert compared against the group, surpassing the 90% agreement milestone set out in the project plan. FIG. 9 illustrates the comparison and the table below provides further information by scenario. As shown, it was found that the AFAS recall rate was 22% better than the average of human experts, and 7% better than the two best expert evaluations used. Thus, it can be concluded that an automated environmental hazard system as disclosed herein may provide improved accuracy and reliability compared to conventional techniques of evaluating an environment for potential hazards such as fall hazards.

| Scenario | Total hazards | A | B | C | D | E | F | Avg. | AFAS avg. |
| --- | --- | --- | --- | --- | --- | --- | --- | --- | --- |
| 1 | 4 | 75.0% | 75.0% | 50.0% | 25.0% | 100.0% | 75.0% | 66.7% | 75.0% |
| 2 | 10 | 50.0% | 60.0% | 40.0% | 80.0% | 60.0% | 60.0% | 58.3% | 80.0% |
| 3 | 10 | 60.0% | 60.0% | 40.0% | 70.0% | 60.0% | 40.0% | 55.0% | 80.0% |
| 4 | 2 | 100.0% | 100.0% | 100.0% | 100.0% | 100.0% | 100.0% | 100.0% | 50.0% |
| 6 | 8 | 100.0% | 62.5% | 50.0% | 50.0% | 75.0% | 75.0% | 68.8% | 87.5% |
| 7 | 5 | 80.0% | 40.0% | 20.0% | 80.0% | 80.0% | 60.0% | 60.0% | 60.0% |
| Total | 39 | 71.8% | 61.5% | 43.6% | 66.7% | 71.8% | 61.5% | 62.8% | 76.9% |

Figure 10:
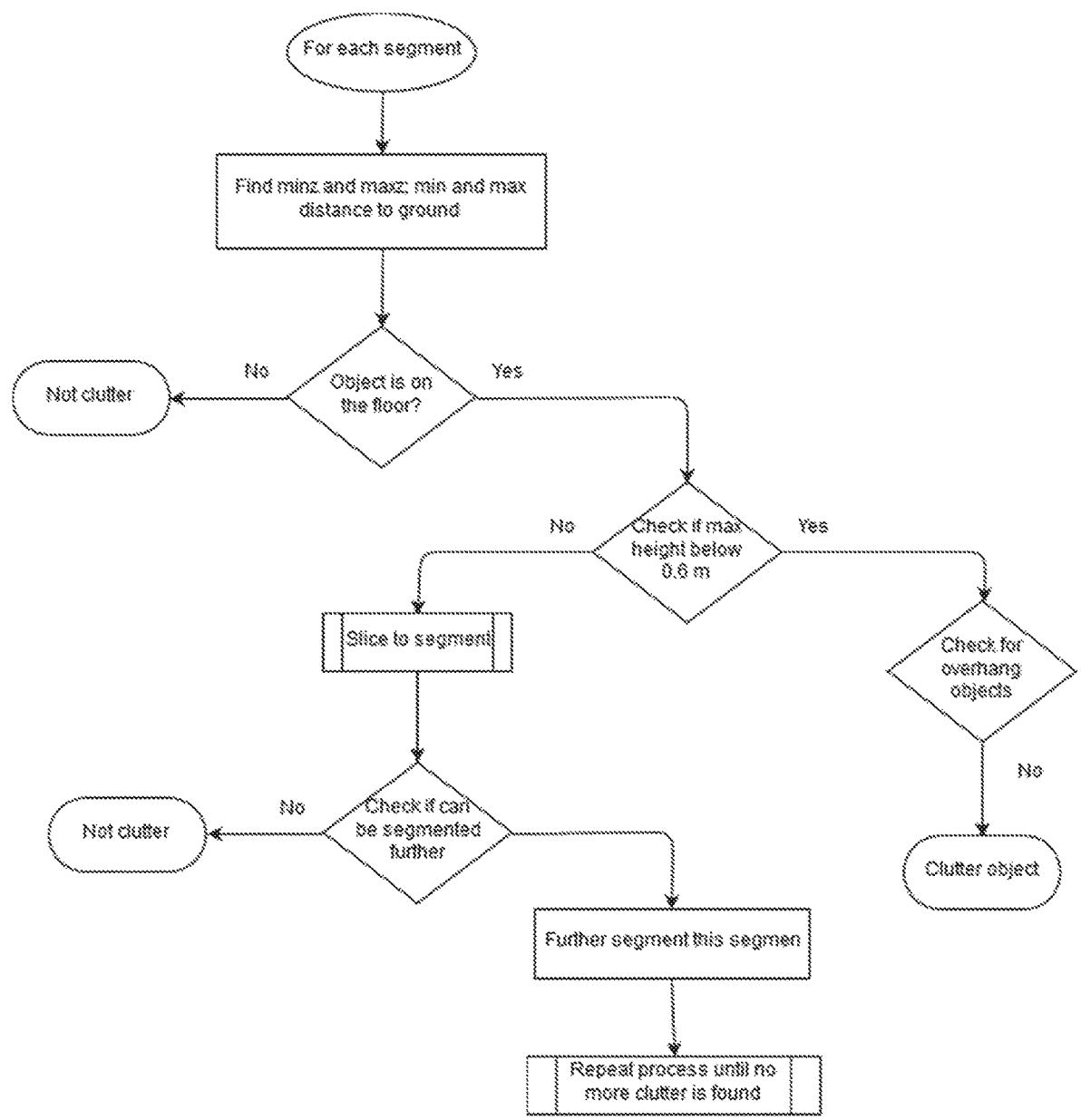
FIG. 10 shows an example of a segmentation technique according to an embodiment of the invention.
Figure 11:
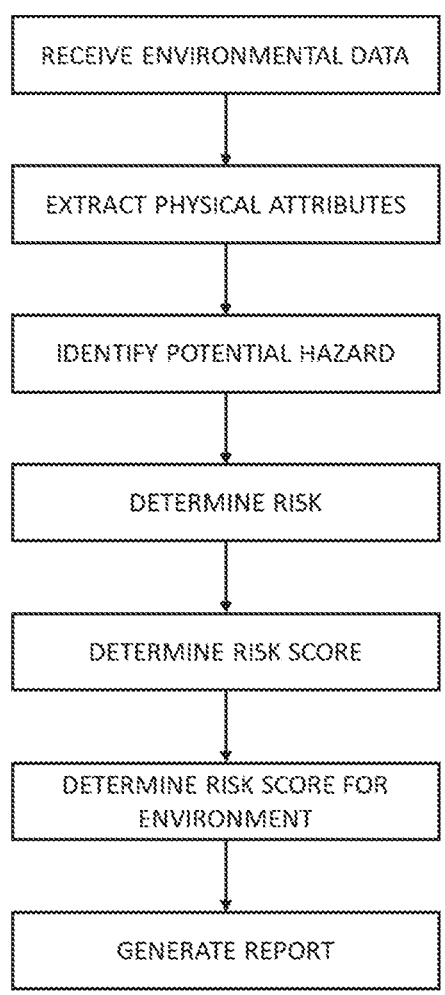
FIG. 11 shows an example process according to an embodiment of the invention.

An example clutter detection algorithm as disclosed herein was also tested. In this example, "clutter" was defined by objects that are less than 24 inch in height. For this test, the PCL VoxelGrid class in the Point Cloud Library was used. More generally, any point cloud or similar analysis technique may be used. To reduce processing time, the point cloud was downsampled using a voxel size of 1 by 1 by 1 cm. A 3D voxel grid was created over the input point cloud data. Then, in each voxel (i.e., 3D box), all the points present were approximated (i.e., downsampled) with their centroid. Part of the point cloud was removed, and only an "area of interest" was retained including the area in front of the sensor platform. In this example, a cart-based sensor platform as previously disclosed was used. Outliers were removed by applying a statistical filter The point cloud was then rotated so that the center of the point cloud was on the ground level below the 3D sensor, and not at the center of the camera. Points matching the ground level were removed, as previously disclosed. The point cloud was then segmented into small segments using the function that segments the point cloud into a series of small point clouds based on the Euclidean distance, i.e. each point cloud that is disconnected from its neighbors is cut. The algorithm used was the following:

1. create a Kd-tree representation for the input point cloud dataset P;
2. set up an empty list of clusters C, and a queue of the points that need to be checked Q;
3. then for every point $p_i \in P$, perform the following steps:
   add $p_i$ to the current queue Q;
   for every point $p_i \in Q$ do:
   search for the set $P_k^i$ of point neighbors of $p_i$ in a sphere with radius $r < d_{th}$;
   for every neighbor $P_k^i \in P_i^k$, check if the point has already been processed, and if not add it to Q;
   when the list of all points in Q has been processed, add Q to the list of clusters C, and reset Q to an empty list
4. the algorithm terminates when all points $p_i \in P$ have been processed and are now part of the list of point clusters C Next, an algorithm as shown in FIG. 10 was applied. The process "slice to segment" as shown in FIG. 10 was applied as follows:

1. Slice the point cloud of interest into points which are above clutter level (0.6 m) call it point cloud A and points below clutter level call it B.
2. Project A and B onto the ground level and call the resulting point clouds A' and B'
3. If Area(B')>Area(A') then; define point cloud C as, each point that belongs to B'-A'
4. Check all the resulting point clouds if they are part of the large objects. This is done by checking the matching between the "shape" of the sliced point cloud and the original point cloud. The matching score is computed by finding the best plane that matches the wall and compare it with the sliced point cloud.
5. Merge with the original if the area representing the segments matches the wall.

This algorithm may be used, for example, to separate small objects that are attached to a larger objects such as a wall.

To determine how to measure changes in height properly with a dedicated topology sensor as disclosed herein, experiments and measurements were performed, and it was determined that a dedicated topology sensor as disclosed herein likely detects a change of 90 units, which equates to approximately half an inch. For each room to be analyzed by an AFAS as disclosed herein, a calibration step may be performed for all sensors which includes finding the average baseline value for the current room flooring. Given that as the sensor moves further from the ground the values returned decrease, averaged return results of 90 units or more less than the calibrated baseline value then indicate hazardous floor transitions.

Similar to the approach taken for floor transition detections, experiments were performed to determine thresholds to use for an ambient light sensor for detecting low lighting. It was determined that values of 2 or less accurately identified low lighting areas.

In other tests, it was determined that one reason for false positives is missing data. For example, it was determined that in a point cloud analysis each point cloud may be analyzed individually without adding any tracking information to the next point cloud. Such a technique may cause false detection of clutter or pathways when there are missing data. Situations in which missing data is expected may be treated by adding another layer of information from the same sensor at a closer distance. This also may be addressed in practice by performing a registration step before analyzing any point cloud. For example, before analyzing a living room, a piecewise registration of point clouds may be performed. An example piecewise registration process may use an iterative closest point technique, such as the following:

1. Find key point features
2. Find the correspondence between the two features
3. Reject bad correspondence
4. Estimate a transformation using the good correspondences.
5. Iterate.
6. Transform the two pairs into the global coordinates As previously disclosed, one technique for detecting a floor transition is the use of a topology sensor assisted by an RGB sensor, for example by using a combination of topology sensor detection plus 2D K-means algorithm applied to the RGB image to separate a floor into two types of floors when hitting a floor transition. Alternatively, it was found that the topology sensor may be used alone. For example, in some cases it was found that using a K-means technique may be relatively unreliable to detect floor transitions, whereas the topology sensor alone was found to be relatively reliable.

In another test, a DFT (Discrete Fourier Transformation) was used to detect the texture of a floor:

$$F(k, l) = \sum_{i=0}^{N-1} \sum_{j=0}^{N-1} f(i, j) e^{-i2\pi\left(\frac{ki}{N} + \frac{ij}{N}\right)}$$

$$e^{ix} = \cos x + i \sin x$$

It was found that such an approach produced acceptable results in cases where the carpet or other flooring has a repetitive pattern. However, the accuracy may be significantly reduced if the flooring has different patterns.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

The invention claimed is:
1. A system comprising:
one or more environmental sensors including at least a camera, each environmental sensor of the one or more environmental sensors configured to obtain environmental data describing at least one physical attribute of an environment in which the system is disposed, the environmental data including at least image data obtained by the camera;

a processing system configured to receive the environmental data from the one or more environmental sensors and, based upon the environmental data, identify at least one potential fall hazard in the environment and a degree of risk associated with the at least one potential fall hazard; and a reporting component configured to provide an indication of the identified at least one potential fall hazard and the degree of risk associated with the fall hazard.

2. The system of claim 1, wherein the system comprises a portable computing device, the portable computing device comprising the one or more environmental sensors, the processing system, and the reporting component.

3. The system of claim 2, wherein the reporting component comprises a display screen.

4. The system of claim 2, wherein the portable computing device is selected from a group consisting of: a tablet, a smart phone, and a portable general-purpose computer.

5. The system of claim 1, wherein the camera comprises an RGB camera configured to capture the image data of the environment.

6. The system of claim 5, wherein the processing system is configured to identify a floor transition, an item of clutter, or both based upon the image data.

7. The system of claim 1, wherein the one or more environmental sensors comprises a topology sensor configured to collect topological data about the environment, and wherein the processing system is configured to identify a floor transition as the identified at least one potential fall hazard based upon the topological data.

8. The system of claim 1, wherein the one or more environmental sensors comprises an ambient light sensor, and wherein the processing system is configured to identify a low light condition as the identified at least one potential fall hazard based upon ambient light data collected by the ambient light sensor.

9. The system of claim 1, wherein the processing system is configured to implement a neural network to identify the at least one potential fall hazard based upon the environmental data, wherein the neural network is trained based upon historic environmental data.

10. The system of claim 1, comprising:
a portable computing device, wherein the portable computing device comprises the one or more environmental sensors; and
a network communication interface, configured to provide the environmental data to the processing system.

11. A method comprising:
receiving, from each of one or more environmental sensors, environmental data describing an environment in which the one or more environmental sensors is disposed;
extracting, from the environmental data, one or more physical attributes of the environment;
based upon the one or more physical attributes, automatically identifying at least one potential hazard in the environment;
based upon the one or more physical attributes, automatically determining a degree of risk associated with the at least one potential hazard;
determining a risk score for a portion of the environment in which the physical attributes are located based upon properties of the environment;
determining a total risk score for the environment based upon the degree of risk associated with the at least one potential hazard and the risk score for the portion of the environment; and
automatically generating a report indicating a presence of the at least one potential hazard, the degree of risk associated with the at least one potential hazard, and the total risk score for the area.

12. The method of claim 11, wherein the one or more environmental sensors are disposed within a portable computing device.

13. The method of claim 12, further comprising automatically displaying the report on a display screen of the portable computing device.

14. The method of claim 12, wherein the portable computing device is selected from a group consisting of: a tablet, a smart phone, and a portable general-purpose computer.

15. The method of claim 11, wherein the one or more environmental sensors comprises an RGB camera configured to capture image data of the environment, and wherein at least one of the one or more physical attributes is determined based upon the image data.

16. The method of claim 15, wherein the step of identifying the at least one potential hazard comprises identifying a floor transition, an item of clutter, or both based upon the image data.

17. The method of claim 11, wherein the one or more of environmental sensors comprises a topology sensor configured to collect topological data about the environment, and wherein the step of identifying the at least one potential hazard comprises identifying a floor transition as the at least one potential hazard based upon the topological data.

18. The method of claim 11, wherein the one or more of environmental sensors comprises an ambient light sensor, and wherein the step of identifying the at least one potential hazard comprises identifying a low light condition as the at least one potential hazard based upon ambient light data collected by the ambient light sensor.

19. The method of claim 11, wherein the step of automatically identifying the at least one potential hazard, the step of automatically determining the degree of risk, or both, is performed by an artificial neural network.

20. The method of claim 11, further comprising providing the environmental data to a remote computing platform, wherein the remote computing platform generates the report.

* * * * *